(12) United States Patent
Jain et al.

(10) Patent No.: US 9,814,423 B2
(45) Date of Patent: Nov. 14, 2017

(54) METHOD AND SYSTEM FOR MONITORING PAIN OF USERS IMMERSED IN VIRTUAL REALITY ENVIRONMENT

(71) Applicants: Lakshya Jain, Los Altos, CA (US); Priya Bisarya, San Diego, CA (US)

(72) Inventors: Lakshya Jain, Los Altos, CA (US); Priya Bisarya, San Diego, CA (US)

( * ) Notice: Subject to any disclaimer, the term of this patent is extended or adjusted under 35 U.S.C. 154(b) by 303 days.

(21) Appl. No.: 14/835,720

(22) Filed: Aug. 26, 2015

(65) Prior Publication Data
US 2017/0055900 A1    Mar. 2, 2017

(51) Int. Cl.
*A61B 5/00*    (2006.01)
*A61B 5/0205*    (2006.01)
*G06T 19/00*    (2011.01)

(52) U.S. Cl.
CPC ........ *A61B 5/4824* (2013.01); *A61B 5/02055* (2013.01); *A61B 5/7246* (2013.01); *A61B 5/744* (2013.01); *G06T 19/006* (2013.01)

(58) Field of Classification Search
CPC . A61B 5/4824; A61B 5/7246; A61B 5/02055; A61B 5/744; G06T 19/006
See application file for complete search history.

(56) References Cited

U.S. PATENT DOCUMENTS

2012/0136274 A1*    5/2012    Burdea .............. A61B 5/04842
600/545

* cited by examiner

*Primary Examiner* — Christine H Matthews
*Assistant Examiner* — Joshua D Lannu
(74) *Attorney, Agent, or Firm* — Thibault Patent Group (57) ABSTRACT

The present disclosure provides a method and system for monitoring a change in intensity of pain experienced by one or more users using a virtual reality environment. The method includes receiving one or more virtual content corresponding to the virtual reality environment on a virtual reality device, displaying the one or more virtual content corresponding to the virtual reality environment on the virtual reality device to the one or more users during one or more treatments provided to the one or more users, assessing the change in the intensity of pain experienced by the one or more users during the one or more treatments, generating a pain profile for each of the one or more users and determining a co-relation between the change in the intensity of pain experienced by the one or more users and the one or more virtual content viewed by the one or more users.

17 Claims, 3 Drawing Sheets

METHOD AND SYSTEM FOR MONITORING PAIN OF USERS IMMERSED IN VIRTUAL REALITY ENVIRONMENT

TECHNICAL FIELD

The present invention relates to the field of biomedical technology and, in particular, relates to monitoring pain of users immersed in a virtual reality environment.

BACKGROUND

Pain is an unpleasant sensory and emotional experience associated with actual or potential tissue damage. In fact, the pain is a stressor and environment challenge that requires an organism to respond. It is a specific emotion, caused by a stimulus that reflects homeostatic behavioral drive, similar to temperature, itching, hunger, thirst and the like. It may be categorized according to various factors, including type of damage, time for healing and the like. Experience of the pain varies from person to person due to inter-individual variability. Moreover, intensity of the pain varies from cause to cause in the individual. Thus, pain management is an extremely important issue.

In the present scenario, a method which has gained a great amount of attention in field of biomedical technology is virtual reality therapy. Many medical professionals have started to make use of a virtual reality environment for treating patients suffering from the pain. The virtual reality environment is an artificial environment created using computer systems and sensory simulation devices including visual displays, audio, motion devices and the like. The medical professionals immerse the patients in a virtual reality by using a virtual reality system. Moreover, the virtual reality system combines two or three dimensional images with audio stimuli for creating the virtual reality environment. The virtual reality environment is produced by utilizing a graphic generating computer, a head mounted display with a tracking device, sensory input devices and the like.

The virtual reality systems have been around for a long time. In addition, the virtual reality systems have found various applications in the field of health care and the pain management. The virtual reality systems are used for various medical applications such as computer aided surgery, wheel chair with the virtual reality system, repetitive strain injury and the like. The concept of virtual reality technology was first used for treatment of acrophobia in 1993. Moreover, in the present time, one such method and system that measures the patient's emotions by using one or more sensors is HumanSim system. Another method and system allows the medical professionals to utilize the virtual reality technology for arriving at a particular diagnosis. Yet another method and system allows the medical professionals to conduct a robotic surgery by using the virtual reality technology. Yet another method and system allows the medical professionals to treat soldiers suffering from Post Traumatic Stress Disorder by immersing the soldiers in stress due to war in the virtual reality environment. Several other present systems are known in the art that utilize the virtual reality technology for treatment of the patients. One such system is presented in U.S. Pat. No. 5,546,943 which proposes a use of the virtual reality system for allowing the patient to view their internal anatomy based on data of their medical scan. Another such method and system allows the doctors to reduce the pain of the patients by immersing the patient in a video game virtual reality environment.

The existing methods and systems for treatment of the pain of the patients using the virtual reality technology are not quite feasible. The existing methods and systems do not allow the medical professionals to measure an effect of viewing of virtual reality content on perception of the pain by the patients. Further, the existing methods and systems do not provide information relating to category or types of the patients experiencing a reduction in the pain while viewing the virtual reality content in the virtual reality environment. In addition, the existing methods and systems do not utilize one or more sensors properly for judging an effect of the virtual content on intensity of the pain of the patients. Moreover, the existing methods and systems do not provision the medical professionals to know whether the virtual reality system is truly effective for treatment of the patients or not.

In light of the above stated discussion, there is a need for a method and system that overcomes the above stated disadvantages.

SUMMARY

In an aspect of the present disclosure, a computer-implemented method for monitoring a change in intensity of pain experienced by one or more users using a virtual reality environment is provided. The one or more users wear a virtual reality device. The computer-implemented method includes receiving, with a processor, one or more virtual content corresponding to the virtual reality environment on a virtual reality device; displaying, with the processor, the received one or more virtual content corresponding to the virtual reality environment on the a virtual reality device to the one or more users during one or more treatments provided to the one or more users; assessing, with the processor, the change in the intensity of pain experienced by the one or more users during the one or more treatments; generating, with the processor, a pain profile for each of the one or more users and determining, with the processor, a co-relation between the change in the intensity of pain experienced by the one or more users during the one or more treatments and the one or more virtual content viewed by the one or more users. The virtual reality device is associated with a pain monitoring application. The assessing is performed on a set of pain monitoring scales using a plurality of bio-markers associated with the one or more users. The set of pain monitoring scales is utilized based on an age category for each of the one or more users. The plurality of bio-markers is measured by a plurality of bio-sensors. The generated pain profile shows the change in the intensity of pain experienced by the one or more users. The pain profile for each of the one or more users is viewed by other one or more users on a corresponding plurality of communication devices. The co-relation represents an effect of the one or more virtual content on the intensity of pain of the one or more users.

In an embodiment of the present disclosure, the computer-implemented method further includes categorizing, with the processor, the one or more users based on the change in the intensity of pain of the one or more users and characteristics of the one or more users. Examples of the characteristics of the one or more users utilized for the categorizing include age, gender, mentality, other one or more physical characteristics (for example, weight and height), Body Mass Index, family history or behavior of the one or more users during the one or more treatments.

In another embodiment of the present disclosure, the computer-implemented method further includes storing, with the processor, the one or more virtual content viewed by the one or more users, the characteristics of the one or more users, the generated pain profile of the one or more users and the plurality of bio-markers associated with the one or more users.

In an embodiment of the present disclosure, the one or more virtual content includes one or more video content, one or more image content, one or more text content and one or more graphic content.

In an embodiment of the present disclosure, the plurality of bio-markers includes heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography (EEG), muscle activity (EMG), accelerometer, EOG, temperature, blood glucose, systolic contraction, systemic resistance and cardiac output. Each of the plurality of bio-markers is projected on one or more screens for viewing by the other one or more users In an embodiment of the present disclosure, the plurality of bio-sensors includes a finger based pulse oximeter, an accelerometer, a respiration monitor, a non-evasive glucose sensor and a 1-lead disposable electrocardiography (ECG) patch.

In an embodiment of the present disclosure, a first type of pain monitoring scales from the set of pain monitoring scales is utilized for assessing the change in the intensity of pain for a first set of users of the one or more users belonging to the age category of adult patients. The first type of pain monitoring scales includes any accepted pain scale including a Visual Analog Scale (VAS), a Verbal Numeric Rating Scale (VNRS), a Brief Pain inventory (BPI), a behavioral pain scale (BPS), a descriptor differential scale (DDS), a dolorimeter pain index (DPI), a neck pain and disability scale and a Visual Descriptive System (VDS).

In an embodiment of the present disclosure, a second type of pain monitoring scales from the set of pain monitoring scales is utilized for assessing the change in the intensity of pain for a second set of users of the one or more users belonging to the age category of pediatric patients. The second type of pain monitoring scales includes any accepted pediatric pain monitoring scale including a physician defined scale, a neonatal pain agitation and sedation scale (N-PASS), a pain assessment tool (PAT), a bernese pain scale for one or more neonates (BPSN), a Wong-Baker scale and a face, legs, activity, crying, and consolability (FLACC) scale.

In another aspect of the present disclosure, a computer system is provided. The computer system includes a non-transitory computer readable medium storing a computer readable program; the computer readable program when executed on a computer causes the computer to perform steps. The steps include receiving one or more virtual content corresponding to a virtual reality environment on a virtual reality device, displaying the received one or more virtual content corresponding to the virtual reality environment on the virtual reality device to one or more users during one or more treatments provided to the one or more users, assessing a change in intensity of pain experienced by the one or more users during the one or more treatments, generating a pain profile for each of the one or more users and determining a co-relation between the change in the intensity of pain experienced by the one or more users during the one or more treatments and the one or more virtual content viewed by the one or more users. The virtual reality device is associated with a pain monitoring application. The assessing is performed on a set of pain monitoring scales using a plurality of bio-markers associated with the one or more users. The set of pain monitoring scales is determined and utilized based on an age category for each of the one or more users. The plurality of bio-markers is measured by a plurality of bio-sensors. The generated pain profile shows the change in the intensity of pain experienced by the one or more users. The pain profile for each of the one or more users is viewed by other one or more users on a corresponding plurality of communication devices. The co-relation represents an effect of the one or more virtual content on the intensity of pain of the one or more users.

In an embodiment of the present disclosure, the computer readable program when executed on the computer causes the computer to perform a further step of categorizing the one or more users based on the change in the intensity of pain of the one or more users and characteristics of the one or more users. The characteristics of the one or more users utilized for the categorizing include age, gender, mentality, other one or more physical characteristics (for example, weight and height), Body Mass Index, family history or behavior of the one or more users during the one or more treatments.

In another embodiment of the present disclosure, the computer readable program when executed on the computer causes the computer to perform a further step of storing the one or more virtual content viewed by the one or more users, the characteristics of the one or more users, the generated pain profile of the one or more users and the plurality of bio-markers associated with the one or more users.

In an embodiment of the present disclosure, the one or more virtual content includes one or more video content, one or more image content, one or more text content and one or more graphic content.

In an embodiment of the present disclosure, the plurality of bio-markers includes heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography (EEG), muscle activity (EMG), accelerometer, EOG, temperature, blood glucose, systolic contraction, systemic resistance and cardiac output. Each of the plurality of bio-markers is projected on one or more screens for viewing by the other one or more users In yet another aspect of the present disclosure, a system for monitoring a change in intensity of pain experienced by one or more users using a virtual reality environment is provided. The system includes a virtual reality device provided to the one or more users for viewing one or more virtual content during one or more treatments and a communication device. The communication device further includes a pain monitoring application to monitor the change in the intensity of pain experienced by the one or more users. The pain monitoring application further includes a receiving module in a processor, the receiving module is configured to receive the one or more virtual content corresponding to the virtual reality environment on the virtual reality device; a display module in the processor, the display module is configured to display the received one or more virtual content corresponding to the virtual reality environment on the virtual reality device to the one or more users during the one or more treatments provided to the one or more users; a diagnostic engine in the processor, the diagnostic engine is configured to assess the change in the intensity of pain experienced by the one or more users during the one or more treatments; an output engine in the processor, the output engine is configured to generate a pain profile for each of the one or more users and a determination module in the processor, the determination module is configured to determine a co-relation between the change in the intensity of pain experienced by the one or more users during the one or more treatments and the one or more virtual content viewed by the one or more users. The one or more virtual content is received from a virtual reality system. The assessing is performed on a set of pain monitoring scales using a plurality of bio-markers associated with the one or more users. The set of pain monitoring scales is determined and utilized based on an age category for each of the one or more users. The plurality of bio-markers is measured by a plurality of bio-sensors. The generated pain profile shows the change in the intensity of pain experienced by the one or more users. The pain profile for each of the one or more users is viewed by other one or more users on a corresponding plurality of communication devices. The co-relation represents an effect of the one or more virtual content on the intensity of pain of the one or more users.

In an embodiment of the present disclosure, the system further includes a categorization module in the processor, the categorization module is configured to categorize the one or more users based on the change in the intensity of pain of the one or more users and characteristics of the one or more users. The characteristics of the one or more users utilized for the categorizing include age, gender, mentality, other one or more physical characteristics (for example, weight and height), Body Mass Index, family history or behavior of the one or more users during the one or more treatments.

In another embodiment of the present disclosure, the system further includes a database in the processor, the database is configured to store the one or more virtual content viewed by the one or more users, the characteristics of the one or more users, the generated pain profile of the one or more users and the plurality of bio-markers associated with the one or more users.

In an embodiment of the present disclosure, the one or more virtual content includes one or more video content, one or more image content, one or more text content and one or more graphic content.

In an embodiment of the present disclosure, the plurality of bio-markers includes heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography (EEG), muscle activity (EMG), accelerometer, EOG, temperature, blood glucose, systolic contraction, systemic resistance and cardiac output. Each of the plurality of bio-markers is projected on one or more screens for viewing by the other one or more users In an embodiment of the present disclosure, a first type of pain monitoring scales from the set of pain monitoring scales is utilized for assessing the change in the intensity of pain for a first set of users of the one or more users belonging to the age category of adult patients. The first type of pain monitoring scales includes any accepted pain scale including a Visual Analog Scale (VAS), a Verbal Numeric Rating Scale (VNRS), a Brief Pain inventory (BPI), a behavioral pain scale (BPS), a descriptor differential scale (DDS), a dolorimeter pain index (DPI), a neck pain and disability scale and a Visual Descriptive System (VDS).

In an embodiment of the present disclosure, a second type of pain monitoring scales from the set of pain monitoring scales is utilized for assessing the change in the intensity of pain for a second set of users of the one or more users belonging to the age category of pediatric patients. The second type of pain monitoring scales includes any accepted pediatric pain monitoring scale including a physician defined scale, a neonatal pain agitation and sedation scale (N-PASS), a pain assessment tool (PAT), a bernese pain scale for one or more neonates (BPSN), a Wong-Baker scale and a face, legs, activity, crying, and consolability (FLACC) scale.

BRIEF DESCRIPTION OF THE FIGURES

Having thus described the invention in general terms, reference will now be made to the accompanying drawings, which are not necessarily drawn to scale, and wherein:

DETAILED DESCRIPTION

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced item.

Figure 1:
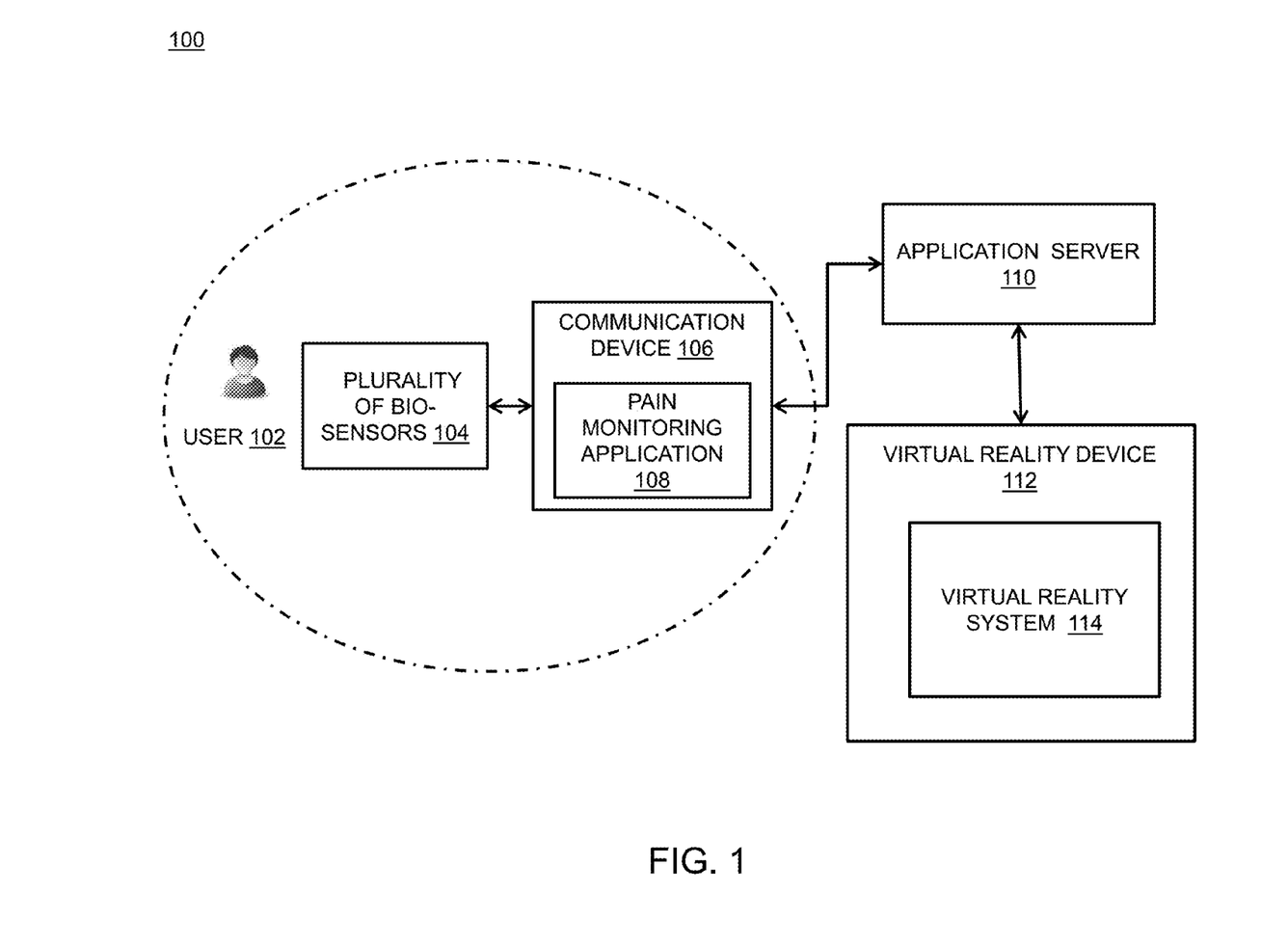
FIG. 1 illustrates a system for monitoring a change in intensity of pain of one or more users, in accordance with various embodiments of the present disclosure.

FIG. 1 illustrates a system 100 for showing an interaction among various components for monitoring a change in intensity of pain experienced by one or more users using a virtual reality environment, in accordance with various embodiments of the present disclosure. The system 100 includes a plurality of bio-sensors 104, a communication device 106 associated with a user 102, an application server 110, a virtual reality device 112 and a virtual reality system 114. The user 102 may be a healthy individual or a patient suffering from the pain. Further, the user 102 is associated with the plurality of bio-sensors 104. The plurality of bio-sensors 104 fetch a plurality of bio-markers associated with the user 102 in real time.

The plurality of bio-sensors 104 include but may not be limited to a finger based pulse oximeter, an accelerometer, a respiration monitor, a non-evasive glucose sensor and a 1-lead disposable electrocardiography (ECG) patch. The plurality of bio-markers includes markers such as heart rate (hereinafter 'HR'), heart rate variability (hereinafter 'HRV'), blood flow, blood pressure (hereinafter 'BP'), movements due to shifts in central blood mass and myocardial electrophysiological responses, respiration information, emotions, skin conductance, Photoplethysmography (hereinafter 'PPG'), oxygen saturation, electrocardiography (hereinafter 'ECG'), electroencephalography (hereinafter 'EEG'), muscle activity (hereinafter 'EMG'), accelerometer, EOG, temperature, blood glucose, systolic contraction, systemic resistance, cardiac output, and the like.

In addition, the communication device 106 is associated with the user 102. Examples of the communication device 106 include but may not be limited to mobile phone, tablet, laptop and desktop computer. The communication device 106 executes a pain monitoring application 108. The pain monitoring application 108 monitors the pain of the user 102 and allows tailoring of treatments accordingly. The pain monitoring application 108 communicates with the application server 110 via a communications network. The communications networks include but may not be limited to a local area network, a wide area network, a metropolitan area network, a virtual private network, a personal area network, a digital or analog cable television network or any other communication network presently known in the art.

Variability in the plurality of bio-markers associated with the user 102 corresponds to autonomic reactions. These symptoms (the autonomic reactions) are analyzed by the pain monitoring application 108 to analyze location and the intensity of the pain in body of the user 102. In addition, the pain monitoring application 108 generates a preliminary pain profile for the user 102 based on the fetched plurality of bio-markers by the plurality of bio-sensors 104. In an embodiment of the present disclosure, the preliminary pain profile depicts the intensity of the pain corresponding to the user 102. The preliminary pain profile depicts the intensity of the pain of the user 102 currently not immersed in the virtual reality environment.

Further, the application server 110 is associated with the virtual reality device 112. The virtual reality device 112 includes but may not be limited to Google glass, Oculus VR, Virtual Boy, Sega VR, Head mounted display, Data glove or any other wearable device capable of displaying a virtual reality scene to the user 102. In an embodiment of the present disclosure, the virtual reality device 112 is provided to the user 102 of the one or more users during one or more treatments corresponding to a medical condition of the user 102.

In addition, the virtual reality device 112 is associated with the virtual reality system 114. The virtual reality device 112 provides one or more virtual content to the user 102. The one or more virtual content corresponds to the virtual reality environment. The virtual reality system 114 includes but may not be limited to an Immersive virtual reality system, Window on the world, Real time Tele presence and augmented virtual reality. In an embodiment of the present disclosure, the virtual reality environment corresponds to an artificial environment shown to the user 102 during the one or more treatments. In an embodiment of the present disclosure, the virtual reality system 114 provides the one or more virtual content to the user 102 on the virtual reality device 112. The one or more virtual content includes one or more video content, one or more image content, one or more graphics content and the like.

In an embodiment of the present disclosure, the application server 110 is associated with the virtual reality system 114 through the virtual reality device 112. In another embodiment of the present disclosure, the pain monitoring application 108 is associated with the virtual reality system 114 through the application server 110. The virtual reality system 114 provides the one or more virtual content to the pain monitoring application 108.

It may be noted that in FIG. 1, the pain monitoring application 108 facilitates the monitoring of the change in the intensity of the pain of the user 102; however, those skilled in the art would appreciate that the pain monitoring application 108 facilitates the monitoring of the change in the intensity of the pain of more users. It may also be noted that the user 102 is associated with the communication device 106; however, those skilled in the art would appreciate that the user 102 may be associated with more than one communication devices having the pain monitoring application 108 installed. It may also be noted that the virtual reality system 114 provides the one or more virtual content to the user 102; however, those skilled in the art would appreciate that the virtual reality system 114 provides the one or more virtual content to more users.

Figure 2:
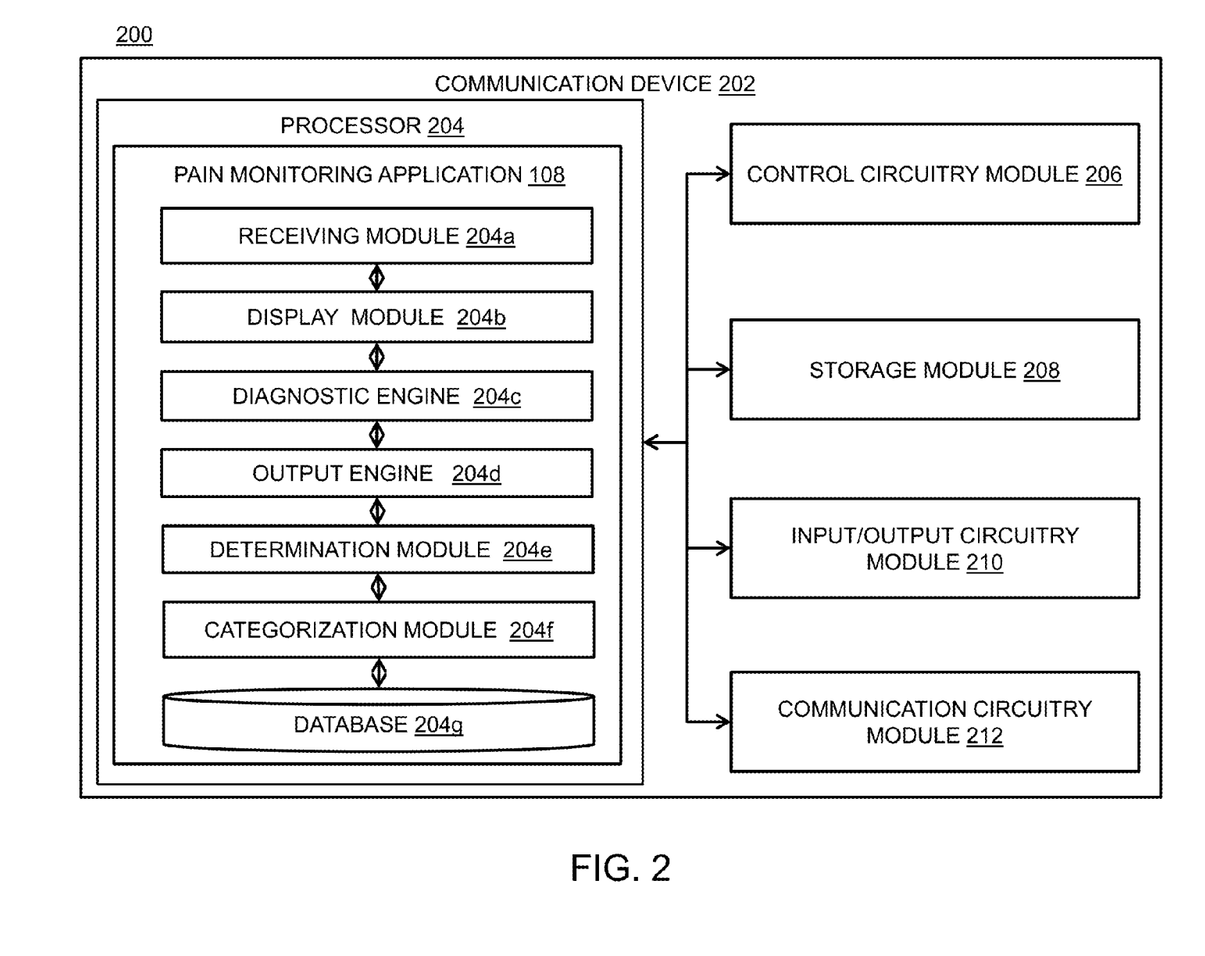
FIG. 2 illustrates a block diagram of a communication device, in accordance with various embodiments of the present disclosure.

FIG. 2 illustrates a block diagram 200 of a communication device 202, in accordance with various embodiments of the present disclosure. It may be noted that to explain the system elements of FIG. 2, references will be made to the system elements of FIG. 1. The communication device 202 includes a processor 204, a control circuitry module 206, a storage module 208, an input/output circuitry module 210 and a communication circuitry module 212. Further, the processer 204 includes a receiving module 204a, a display module 204b, a diagnostic engine 204c, an output engine 204d, a determination module 204e, a categorization module 204f and a database 204g. The above stated components of the processor 204 enable working of the pain monitoring application 108 for monitoring the change in the intensity of the pain experienced by the user 102 using the virtual reality environment displayed on the virtual reality device 112 during the one or more treatments.

The receiving module 204a in the processor 204 receives the one or more virtual content corresponding to the virtual reality environment on the virtual reality device 112. The one or more virtual content is received during the one or more treatments on the virtual reality device 112. In an embodiment of the present disclosure, the one or more virtual content is received from the virtual reality system 114. The one or more virtual content corresponds to the virtual reality environment. In an embodiment of the present disclosure, the virtual reality environment is the artificial environment created by the virtual reality system 114 provided to the user 102 during the one or more treatments.

The display module 204b in the processor 204 displays the received one or more virtual content corresponding to the virtual reality environment to the user 102 through the virtual reality device 112 during the one or more treatments. The user 102 views the one or more virtual content on the virtual reality device 112. In an embodiment of the present disclosure, the displayed one or more virtual content is based on characteristics of the user 102. The characteristics of the user 102 include but may not be limited to age of the user 102, gender of the user 102, popular visiting destinations corresponding to the user 102, popular shows and games corresponding to the user 102 and the like. In an embodiment of the present disclosure, the user 102 is immersed in the virtual reality environment during the one or more treatments. In another embodiment of the present disclosure, the one or more virtual content is displayed for distracting the user 102 from the pain encountered during the one or more treatments.

For example, a user X is a male of age 48 suffering from first stage lung cancer and a user Y is a male of age 12 is suffering from brain tumor. The user X is provided with a chemotherapy treatment for treatment of the lung cancer by a medical practitioner K and the user Y is provided with a radiotherapy treatment for treatment of the brain tumor by a medical practitioner L. The user X and the user Y suffer excruciating pain during the chemotherapy treatment and the radiotherapy treatment. The pain monitoring application 108 generates a pain profile (the preliminary pain profile as stated above in the patent application) for the user X and the user Y. The pain profile depicts a current intensity of the pain experienced by the user X and the user Y. The medical practitioner K provides the user X with a virtual reality device (say Virtual Boy) and the medical practitioner L provides the user Y with a virtual reality device Samsung Gear VR. The user X wears the virtual reality device Virtual Boy and the user Y wears the virtual reality device Samsung Gear VR. The user X views a virtual content in a form of a first scene of his mother in a waiting room and a second scene of a beach near his home on the virtual reality device Virtual Boy. The user Y views a virtual content in a form of a first scene of his favorite movie and a second scene of a religious place the user Y visits on the virtual reality device Samsung Gear VR.

Further, the diagnostic engine 204c in the processor 204 assesses the change in the intensity of the pain experienced by the user 102 during the one or more treatments while viewing the one or more virtual content on the virtual reality device 112. In an embodiment of the present of disclosure, the diagnostic engine 204c fetches the plurality of bio-markers associated with the user 102 by the plurality of bio-sensors 104. In addition, the diagnostic engine 204c performs the assessing on a set of pain monitoring scales using the fetched plurality of bio-markers associated with the user 102. Further, the set of pain monitoring scales are utilized based on an age category of the user 102. The plurality of bio-markers is measured by a plurality of bio-sensors. A change in statistical value of the plurality of bio-markers corresponding to the user 102 depicts the change in the intensity of the pain experienced by the user 102 during the one or more treatments.

In an embodiment of the present disclosure, a first type of pain monitoring scales from the set of pain monitoring scales are utilized for assessing the change in the intensity of pain for a first set of users of the one or more users belonging to the age category of adult patients. In addition, the first type of pain monitoring scales includes any accepted pain scale including a Visual Analog Scale (VAS), a Verbal Numeric Rating Scale (VNRS), a Brief Pain inventory (BPI), a behavioral pain scale (BPS), a descriptor differential scale (DDS), a dolorimeter pain index (DPI), a neck pain and disability scale, a Visual Descriptive System (VDS) and the like.

In an embodiment of the present disclosure, a second type of pain monitoring scales from the set of pain monitoring scales are utilized for assessing the change in the intensity of pain for a second set of users of the one or more users belonging to the age category of pediatric patients. Moreover, the second type of pain monitoring scales includes any accepted pediatric pain monitoring scale including a physician defined scale, a neonatal pain agitation and sedation scale (N-PASS), a pain assessment tool (PAT), a bernese pain scale for one or more neonates (BPSN), a Wong-Baker scale, a face, legs, activity, crying, and consolability (FLACC) scale and the like.

Continuing with the above stated example, the diagnostic engine 204c assesses the change in the intensity of the pain of the user X while viewing the virtual content (the first scene and the second scene) on the virtual reality device Virtual Boy during the chemotherapy treatment and the change in the intensity of the pain of the user Y while viewing the virtual content (the first scene and the second scene) on the virtual reality device Samsung Gear VR during the radiotherapy treatment. The diagnostic engine 204c fetches the plurality of bio-markers associated with the user X and the user Y.

Moreover, the output engine 204d in the processor 204 generates a pain profile for the user 102 while viewing the one or more virtual content during the one or more treatments provided to the user 102. The generated pain profile shows the change in the intensity of the pain experienced by the user 102. Further, the generated pain profile includes the information relating to the plurality of bio-markers fetched by the diagnostic engine 204c. In addition, the pain profile for each of the one or more users is viewed by other one or more users on a corresponding plurality of communication devices. The plurality of communication devices includes a mobile phone, a laptop, a desktop computer and the like. In an embodiment of the present disclosure, the plurality of communication devices enables the other one or more users to assess the intensity of pain experienced by the user 102.

Moreover, the output engine 204d generates the pain profile for the user 102 by analyzing the intensity of the pain experienced by the user 102. In an embodiment of the present disclosure, the intensity of the pain is analyzed for each increment between a former level of the pain and a next level of the pain. In another embodiment of the present disclosure, the pain profile is a newly generated pain profile for the user 102. In another embodiment of the present disclosure, the change in the intensity of the pain is assessed against the intensity of the pain depicted by the preliminary pain profile generated for the user 102 (as described above in the detailed description of FIG. 1). In yet another embodiment of the present disclosure, the previously generated pain profile (the preliminary pain profile) depicts the intensity of the pain when the user 102 is not provided with the virtual reality device 112 for viewing the one or more virtual content.

Extending the above stated example, the output engine 204d generates the pain profile for the user X while viewing the virtual content during the chemotherapy treatment and the pain profile for the user Y while viewing the virtual content during the radiotherapy treatment. The pain profile depicts a statistical change in the intensity of the pain shown by the values of the plurality of bio-markers as compared to the values of the plurality of the bio-markers depicted in the previously generated pain profile (the preliminary pain profile) of the user X and the user Y.

Going further, the determination module 204e in the processor 204 determines a co-relation between the change in the intensity of the pain experienced by the user 102 during the one or more treatments and the one or more virtual content viewed by the user 102. The determining of the co-relation between the change in the intensity of the pain and the one or more virtual content is based on the pain profile generated for the user 102 by the output engine 204d. Further, the determination module 204e determines the co-relation between the change in the intensity of the pain and the one or more virtual content for studying an effect of viewing the one or more virtual content by the user 102 on the intensity of the pain of the user 102.

In an embodiment of the present disclosure, the co-relation between the change in the intensity of the pain and the one or more virtual content depicts an effect of distracting the user 102 by immersing the user 102 in the virtual reality environment on the intensity of the pain of the user 102. The change in the intensity of the pain is depicted by the pain profile generated by the output engine 204d for the user 102.

In an embodiment of the present disclosure, the determination module 204e determines the co-relation between the changed pain profile of the user 102 and the one or more virtual content viewed by the user 102.

Continuing with the above stated example, the determination module 204e determines the co-relation for the user X between the change in the intensity of the pain depicted in the generated pain profile of the user X and the virtual content viewed by the user X on the virtual reality device Virtual Boy. The determination module 204e depicts a significant decrease in the intensity of the pain of the user X while viewing the virtual content (the first scene of his mother in the waiting room and the second scene of the beach near his home). Similarly, the determination module 204e determines the co-relation for the user Y between the change in the intensity of the pain depicted in the generated pain profile of the user Y and the virtual content viewed by the user Y on the virtual reality device Samsung Gear VR. The determination module 204e depicts a slight decrease in the intensity of the pain of the user Y while viewing the virtual content (the first scene of his favorite movie and the second scene of the religious place the user Y visits).

In another embodiment of the present disclosure, the co-relation between the change in the intensity of the pain and the one or more virtual content helps one or more medical practitioners to determine whether the virtual reality system 114 is useful in reducing the intensity of the pain experienced by the user 102. In yet another embodiment of the present disclosure, the co-relation between the change in the intensity of the pain and the one or more virtual content helps in studying the effect of the one or more virtual content on the intensity of the pain of the user 102. In yet another embodiment of the present disclosure, the co-relation is performed for determining a change in perception of the pain of the user 102 and the other one or more users.

For example, a dentist A performs a root canal procedure on a patient B and provides the patient B with a virtual reality device Data Glove. The dentist A places one or more bio-sensors on body of the patient B for measuring one or more bio-markers associated with the patient B. The patient B uses the data glove while going through the root canal treatment. The dentist A recognizes a change in statistical value of the one or more bio-markers associated with the patient B and recognizes a decrease in the pain of the patient B.

In addition, the categorization module 204f in the processor 204 categorizes the user 102 and other one or more users based on the change in the intensity of the pain experienced by the user 102 and the other one or more users and the characteristics of the user 102. In an embodiment of the present disclosure, the categorization module 204f categorizes the user 102 and the other one or more users into one or more groups of users based on the change in the intensity of the pain. In another embodiment of the present disclosure, the categorization of the user 102 and the other one or more users is performed for noticing one or more types of users from the one or users experiencing a decrease in the intensity of the pain. The one or more types of users are categorized based on the characteristics of the user 102 and the other one or more users. The characteristics of the one or more users utilized for the categorizing include age, gender, mentality, other one or more physical characteristics (for example, weight and height), Body Mass Index, family history, behavior of the one or more users during the one or more treatments and the like.

Moreover, the database 204g in the processor stores the generated pain profile of the user 102, the fetched plurality of bio-markers of the user 102, the characteristics of the user 102 and the one or more virtual content viewed by the user 102.

In an embodiment of the present disclosure, the one or more pain monitoring scales are utilized to measure the intensity of the pain experienced by the user 102. The one or more pain monitoring scales include but may not be limited to a visual analog scale (VAS), a Verbal Numeric Rating Scale (VNRS), a Brief Pain inventory (BPI) and a Visual Descriptive System (VDS), a behavior pain scale (BPS), a descriptor differential scale (DDS), a dolorimeter pain index (DPI), a neck pain and disability scale, a physician defined scale, a neonatal pain agitation and sedation scale (N-PASS), a pain assessment tool (PAT), a bernese pain scale for one or more neonates (BPSN), a Wong-Baker scale and a face, legs, activity, crying, and consolability (FLACC) scale. The scales used may vary as deemed appropriate by the physician and may depend upon the age and maturity of the user.

In another embodiment of the present disclosure, the intensity of the pain experienced by the user 102 is increased and measured several times on the user 102 to check consistency of, and improve upon the learned information with new observations. For example, the new observations are generated when the intensity of the pain experienced by the user 102 is increased or decreased again one or more times.

In yet another embodiment of the present disclosure, the method is repeated several times to obtain improved machine learning.

In an embodiment of the present disclosure, each of the plurality of bio-markers is projected on one or more screens for viewing by the other one or more users. In another embodiment of the present disclosure, the projecting is done for allowing the other one or more users to assess the intensity of pain. In an embodiment of the present disclosure, the other one or more users are in vicinity of the user 102. In another embodiment of the present disclosure, the other one or more users are remotely located from the user 102. The other one or more users include one or more doctors, parents or any other person.

In yet another embodiment of the present disclosure, the generated pain profile for the user 102 utilizes a pre-defined color coding based on the intensity and the location of the pain in the body of the user 102. Intensity of the colors increases proportionally with respect to the pain experienced by the user 102. Moreover, the intensity of the colors may differentiate areas in the body of the user 102 that are most susceptible to the pain. Further, the intensity of the colors may segregate affected or bruised areas in the body of the user 102 with healthy areas.

In yet another embodiment of the present disclosure, the pain monitoring application 108 may be used in various fields including dental treatment, medical treatment, sports/athletics, occupational health and the like. For example, a dental hygienist may utilize the pain monitoring application 108 to assist cleaning of patient's teeth.

In yet another embodiment of the present disclosure, the communication device 202 is associated with the plurality of bio-sensors 104 via the network (for e.g., LAN, WAN, MAN, Bluetooth, Wi-Fi and the like). Thus, the communication device 202 collects the inputs relating to the autonomic reactions including the heart rate variability, the galvanic skin response, the amount of pressure applied and the like from the user 102.

In yet another embodiment of the present disclosure, the pain profile for the user 102 is generated by using any combination of sensors from the plurality of bio-sensors 104.

In yet another embodiment of the present disclosure, the intensity of the pain is characterized by tremendous inter-individual variability and is different for different persons. It can be controlled by biological factors (gender, genetics and the like), psychological factors (mood, attention and the like) and social factors (marital status), experimental factors and the like. For example, a patient (user 102) who is experiencing a chronic pain may not report same pain level as those who are new to the pain experience.

In yet another embodiment of the present disclosure, treatment of the user 102 is based on his phenotypical characteristics, genotypical characteristics and mental attributes.

In yet another embodiment of the present disclosure, the virtual reality environment corresponds to a three dimensional, interactive and computer generated reality.

In yet another embodiment of the present disclosure, the virtual reality system 114 controls sensory experience of the user 102.

In yet another embodiment of the present disclosure, the virtual reality system 114 is made up of one or more hardware components and one or more software components. The one or more hardware components include primary interfaces, tracking interfaces, visual interfaces, auditory interfaces, haptic interfaces, olfactory interfaces and the like. The one or more software components include but may not be limited to an input process, simulation process, rendering process and a world database.

Going further, the communication device 202 includes any suitable type of portable electronic device. Examples of the communication device 202 include but may not be limited to a personal e-mail device (e.g., a Blackberry™ made available by Research in Motion of Waterloo, Ontario), a personal data assistant ("PDA"), a cellular telephone, a Smartphone, a handheld gaming device, a digital camera, the laptop computer, and a tablet computer. In another embodiment of the present disclosure, the communication device 202 can be a desktop computer.

From the perspective of this disclosure, the control circuitry module 206 includes any processing circuitry or processor operative to control the operations and performance of the communication device 202. For example, the control circuitry module 206 may be used to run operating system applications, firmware applications, media playback applications, media editing applications, or any other application. In an embodiment, the control circuitry module 206 drives a display and process inputs received from a user interface.

From the perspective of this disclosure, the storage module 208 includes one or more storage mediums including a hard-drive, solid state drive, flash memory, permanent memory such as ROM, any other suitable type of storage component, or any combination thereof. The storage module 208 may store, for example, media data (e.g., music and video files), application data (e.g., for implementing functions on the communication device 202).

From the perspective of this disclosure, the input/output circuitry module 210 may be operative to convert (and encode/decode, if necessary) analog signals and other signals into digital data. In an embodiment, the input/output circuitry module 210 may also convert the digital data into any other type of signal and vice-versa. For example, the input/output circuitry module 210 may receive and convert physical contact inputs (e.g., from a multi-touch screen), physical movements (e.g., from a mouse or sensor), analog audio signals (e.g., from a microphone), or any other input. The digital data may be provided to and received from the control circuitry module 206, the storage module 208 or any other component of the communication device 202.

It may be noted that the input/output circuitry module 210 is illustrated in FIG. 2 as a single component of the communication device 202; however, those skilled in the art would appreciate that several instances of the input/output circuitry module 210 may be included in the communication device 202.

The communication device 202 may include any suitable interface or component for allowing the user 102 to provide inputs to the input/output circuitry module 210. The communication device 202 may include any suitable input mechanism. Examples of the input mechanism include but may not be limited to a button, keypad, dial, a click wheel, and a touch screen. In an embodiment, the communication device 202 may include a capacitive sensing mechanism, or a multi-touch capacitive sensing mechanism.

In an embodiment, the communication device 202 may include specialized output circuitry associated with output devices such as, for example, one or more audio outputs. The audio output may include one or more speakers built into the communication device 202, or an audio component that may be remotely coupled to the communication device 202.

The one or more speakers can be mono speakers, stereo speakers, or a combination of both. The audio component can be a headset, headphones or ear buds that may be coupled to the communication device 202 with a wire or wirelessly.

In an embodiment, the input/output circuitry module 210 may include display circuitry for providing a display visible to the user 102. For example, the display circuitry may include a screen (e.g., an LCD screen) that is incorporated in the communication device 202.

The display circuitry may include a movable display or a projecting system for providing a display of content on a surface remote from the communication device 202 (e.g., a video projector). In an embodiment, the display circuitry may include a coder/decoder to convert digital media data into the analog signals. For example, the display circuitry may include video Codecs, audio Codecs, or any other suitable type of Codec.

The display circuitry may include display driver circuitry, circuitry for driving display drivers or both. The display circuitry may be operative to display content. The display content can include media playback information, application screens for applications implemented on the electronic device, information regarding ongoing communications operations, information regarding incoming communications requests, or device operation screens under the direction of the control circuitry module 206. Alternatively, the display circuitry may be operative to provide instructions to a remote display.

In addition, the communication device 202 includes the communication circuitry module 212. The communication circuitry module 212 may include any suitable communication circuitry operative to connect to a communication network and to transmit communications (e.g., voice or data) from the communication device 202 to other devices within the communications network. The communication circuitry module 212 may be operative to interface with the communication network using any suitable communication protocol. Examples of the communication protocol include but may not be limited to Wi-Fi, Bluetooth RTM, radio frequency systems, infrared, LTE, GSM, GSM plus EDGE, CDMA, and quadband.

In an embodiment, the communication circuitry module 212 may be operative to create a communications network using any suitable communications protocol. For example, the communication circuitry module 212 may create a short-range communication network using a short-range communications protocol to connect to other devices. For example, the communication circuitry module 212 may be operative to create a local communication network using the Bluetooth, RTM protocol to couple the communication device 202 with a Bluetooth, RTM headset.

It may be noted that the computing device is shown to have only one communication operation; however, those skilled in the art would appreciate that the communication device 202 may include one more instances of the communication circuitry module 212 for simultaneously performing several communication operations using different communication networks. For example, the communication device 202 may include a first instance of the communication circuitry module 212 for communicating over a cellular network, and a second instance of the communication circuitry module 212 for communicating over Wi-Fi or using Bluetooth RTM.

In an embodiment, the same instance of the communication circuitry module 212 may be operative to provide for communications over several communication networks. In an embodiment, the communication device 202 may be coupled a host device for data transfers, synching the communication device 202, software or firmware updates, providing performance information to a remote source (e.g., providing riding characteristics to a remote server) or performing any other suitable operation that may require the communication device 202 to be coupled to a host device. Several computing devices may be coupled to a single host device using the host device as a server. Alternatively or additionally, the communication device 202 may be coupled to the several host devices (e.g., for each of the plurality of the host devices to serve as a backup for data stored in the communication device 202).

It may be noted that in FIG. 2, various modules of the pain monitoring application 108 are shown that illustrates the working of the pain monitoring application 108; however, those skilled in the art would appreciate that the pain monitoring application 108 may have more number of modules that could illustrate overall functioning of the pain monitoring application 108. It may also be noted that the output engine 204d generates the pain profile of the user 102; however, those skilled in the art would appreciate that the output engine 204d generates more than one pain profile for more than one user. It may also be noted that the database 204g stores the pain profile of the user 102; however, those skilled in the art would appreciated that the database 204g stores more than one profile for more than one user.

Figure 3:
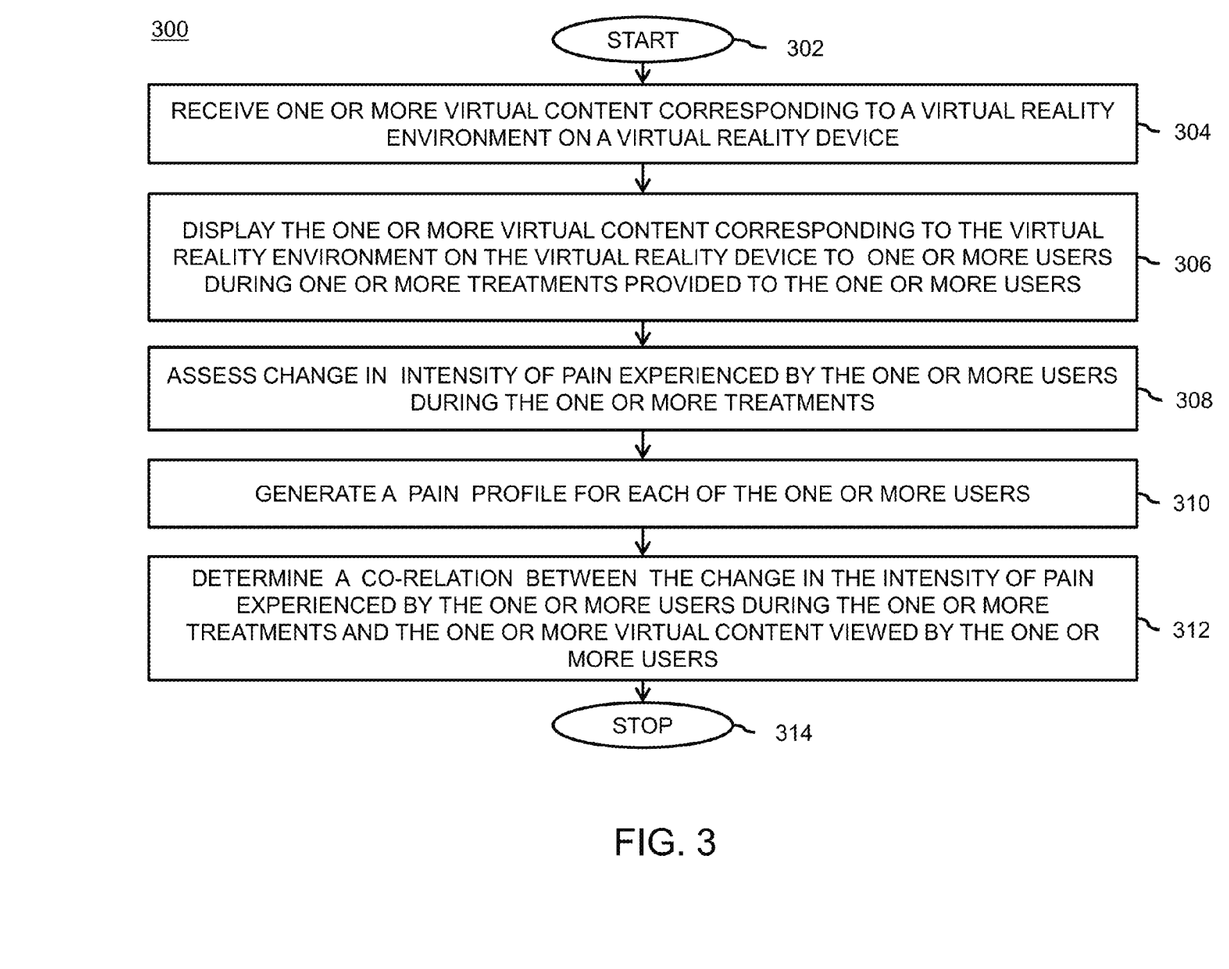
FIG. 3 is a flowchart for monitoring the change in the intensity of the pain of the one or more users, in accordance with the various embodiments of the present disclosure.

FIG. 3 illustrates a flowchart 300 for monitoring the change in the intensity of the pain experienced by the one or more users using the virtual reality environment, in accordance with the various embodiments of the present disclosure. The flowchart 300 initiates at step 302. At step 304, the receiving module 204a receives the one or more virtual content corresponding to the virtual reality environment on the virtual reality device 112. The virtual reality device 112 is associated with the pain monitoring application 108. At step 306, the display module 204b displays the one or more virtual content corresponding to the virtual reality environment on the virtual reality device to the user 102 during the one or more treatments provided to the user 102. At step 308, the diagnostic engine 204c assesses the change in the intensity of the pain experienced by the user 102 during the one or more treatments. At step 310, the output engine 204d generates the pain profile for the user 102. The generated pain profile shows the change in the intensity of the pain experienced by the user 102. At step 312, the determination module 204e determines the co-relation between the change in the intensity of the pain experienced by the user 102 during the one or more treatments and the one or more virtual content viewed by the user 102. The co-relation represents the effect of the one or more virtual content on the intensity of the pain of the user 102. The flowchart 300 terminates at step 314.

It may be noted that the flowchart 300 is explained to have above stated process steps; however, those skilled in the art would appreciate that the flowchart 300 may have more/less number of process steps which may enable all the above stated embodiments of the present disclosure.

While the disclosure has been presented with respect to certain specific embodiments, it will be appreciated that many modifications and changes may be made by those skilled in the art without departing from the spirit and scope of the disclosure. It is intended, therefore, by the appended claims to cover all such modifications and changes as fall within the true spirit and scope of the disclosure.

What is claimed is:

1. A computer-implemented method for monitoring a change in intensity of pain experienced by one or more users using a virtual reality environment, the one or more users wearing a virtual reality device, the computer-implemented method comprising:
   receiving, with a processor, one or more virtual content corresponding to the virtual reality environment on the virtual reality device, wherein the virtual reality device is associated with a pain monitoring application;
   displaying, with the processor, the received one or more virtual content corresponding to the virtual reality environment on the virtual reality device to the one or more users during one or more treatments provided to the one or more users;
   assessing, with the processor, a change in an intensity of pain experienced by the one or more users during the one or more treatments, the assessing being performed on a set of pain monitoring scales using a plurality of bio-markers associated with the one or more users, the set of pain monitoring scales being determined and utilized based on an age category for each of the one or more users and the plurality of bio-markers are measured by a plurality of bio-sensors;
   generating, with the processor, a pain profile for each of the one or more users, the generated pain profile showing the change in the intensity of pain experienced by the one or more users and the pain profile for each of the one or more users is viewed by the one or more users on a corresponding plurality of communication devices; and
   determining, with the processor, a co-relation between the change in the intensity of pain experienced by the one or more users during the one or more treatments and the one or more virtual content viewed by the one or more users, the co-relation representative of an effect of the one or more virtual content on the intensity of pain of the one or more users; and
   storing, with the processor, the one or more virtual content viewed by the one or more users, characteristics of the one or more users, the generated pain profile of the one or more users and the plurality of bio-markers associated with the one or more users.

2. The computer-implemented method as recited in claim 1, further comprising categorizing, with the processor, the one or more users based on the change in the intensity of pain of the one or more users and characteristics of the one or more users, wherein the characteristics of the one or more users utilized for the categorizing comprises age, gender, mentality, Body Mass Index, family history or behavior of the one or more users during the one or more treatments.

3. The computer-implemented method as recited in claim 1, wherein the one or more virtual content comprises one or more video content, one or more image content, one or more text content and one or more graphic content.

4. The computer-implemented method as recited in claim 1, wherein the plurality of bio-markers comprises heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography(EEG), muscle activity (EMG), accelerometer, EOG, temperature, blood glucose, systolic contraction, systemic resistance and cardiac output and wherein each of the plurality of bio-markers is projected on one or more screens for viewing by the other one or more users.

5. The computer-implemented method as recited in claim 1, wherein the plurality of bio-sensors comprises a finger based pulse oximeter, an accelerometer, a respiration monitor, a non-evasive glucose sensor and a 1-lead disposable electrocardiography (ECG) patch.

6. The computer-implemented method as recited in claim 1, wherein a first type of pain monitoring scales from the set of pain monitoring scales is utilized for assessing the change in the intensity of pain for a first set of users of the one or more users belonging to an age category of adult patients, wherein the first type of pain monitoring scales comprises any accepted pain scale comprising a Visual Analog Scale (VAS), a Verbal Numeric Rating Scale (VNRS), a Brief Pain inventory (BPI), a behavioral pain scale (BPS), a descriptor differential scale (DDS), a dolorimeter pain index (DPI), a neck pain and disability scale and a Visual Descriptive System (VDS).

7. The computer-implemented method as recited in claim 1, wherein a second set of pain monitoring scales from the set of pain monitoring scales is utilized for assessing the change in the intensity of pain for a second set of users of the one or more users belonging to an age category of pediatric patients, wherein the second type of pain monitoring scales comprises any accepted pediatric pain monitoring scale comprising a physician defined scale, a neonatal pain agitation and sedation scale (N-PASS), a pain assessment tool (PAT), a bernese pain scale for one or more neonates (BPSN), a Wong-Baker scale and a face, legs, activity, crying, and consolability (FLACC) scale.

8. A computer program product comprising a non-transitory computer readable medium storing a computer readable program, wherein the computer readable program when executed on a computer causes the computer to perform steps comprising:
  receiving one or more virtual content corresponding to a virtual reality environment on a virtual reality device, the virtual reality device associated with a pain monitoring application;
  displaying the received one or more virtual content corresponding to the virtual reality environment on the virtual reality device to one or more users during one or more treatments provided to the one or more users;
  assessing a change in intensity of pain experienced by the one or more users during the one or more treatments, the assessing performed on a set of pain monitoring scales using a plurality of bio-markers associated with the one or more users, the set of pain monitoring scales being determined and utilized based on an age category for each of the one or more users and the plurality of bio-markers are measured by a plurality of bio-sensors;
  generating a pain profile for each of the one or more users, wherein the generated pain profile shows the change in the intensity of pain experienced by the one or more users, the pain profile for each of the one or more users being viewed by the one or more users on a corresponding plurality of communication devices; and
  determining a co-relation between the change in the intensity of pain experienced by the one or more users during the one or more treatments and the one or more virtual content viewed by the one or more users, wherein the co-relation is representative of an effect of the one or more virtual content on the intensity of pain of the one or more users;
  wherein the computer readable program when executed on the computer causes the computer to perform a further step of storing the one or more virtual content viewed by the one or more users, the characteristics of the one or more users, the generated pain profile of the one or more users and the plurality of bio-markers associated with the one or more users.

9. The computer program product as recited in claim 8, wherein the computer readable program when executed on the computer causes the computer to perform a further step of categorizing the one or more users based on the change in the intensity of pain of the one or more users and characteristics of the one or more users, the characteristics of the one or more users utilized for the categorizing comprising age, gender, mentality, Body Mass Index, family history or behavior of the one or more users during the one or more treatments.

10. The computer program product as recited in claim 8, wherein the one or more virtual content comprises one or more video content, one or more image content, one or more text content and one or more graphic content.

11. The computer program product as recited in claim 8, wherein the plurality of bio-markers comprises heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography(EEG), muscle activity (EMG), accelerometer, EOG, temperature, blood glucose, systolic contraction, systemic resistance and cardiac output, each of the plurality of bio-markers being projected on one or more screens for viewing by the other one or more users.

12. A system for monitoring a change in intensity of pain experienced by one or more users using a virtual reality environment the system comprising:
  a virtual reality device provided to the one or more users for viewing one or more virtual content during one or more treatments;
  a communication device, wherein the communication device further comprises a pain monitoring application to monitor a change in the intensity of pain experienced by the one or more users, wherein the pain monitoring application further comprises;
  a receiving module in a processor, the receiving module being configured to receive the one or more virtual content corresponding to the virtual reality environment on the virtual reality device; the one or more virtual content received from a virtual reality system on the virtual reality device;
  a display module in the processor, the display module being configured to display the received one or more virtual content corresponding to the virtual reality environment on the virtual reality device to the one or more users during the one or more treatments provided to the one or more users;

a diagnostic engine in the processor, the diagnostic engine being configured to assess the change in the intensity of pain experienced by the one or more users during the one or more treatments, the assessing performed on a set of pain monitoring scales using a plurality of bio-markers associated with the one or more users, the set of pain monitoring scales being determined and utilized based on an age category for each of the one or more users and the plurality of bio-markers measured by a plurality of bio-sensors;

an output engine in the processor, the output engine being configured to generate a pain profile for each of the one or more users, wherein the generated pain profile shows the change in the intensity of pain experienced by the one or more users and wherein the pain profile for each of the one or more users is viewed by the one or more users on a corresponding plurality of communication devices; and a determination module in the processor, the determination module being configured to determine a co-relation between the change in the intensity of pain experienced by the one or more users during the one or more treatments and the one or more virtual content viewed by the one or more users, wherein the co-relation is representative of an effect of the one or more virtual content on the intensity of pain of the one or more users; and a database in the processor, the database being configured to store the one or more virtual content viewed by the one or more users, the characteristics of the one or more users, the generated pain profile of the one or more users and the plurality of bio-markers associated with the one or more users.

13. The system as recited in claim 12, further comprising a categorization module in the processor, the categorization module being configured to categorize the one or more users based on the change in the intensity of pain of the one or more users and characteristics of the one or more users, the characteristics of the one or more users utilized for the categorizing comprising age, gender, mentality, Body Mass Index, family history or behavior of the one or more users during the one or more treatments.

14. The system as recited in claim 12, wherein the one or more virtual content comprises one or more video content, one or more image content, one or more text content and one or more graphic content.

15. The system as recited in claim 12, wherein the plurality of bio-markers comprises heart rate, heart rate variability (HRV), blood flow, blood pressure, movements due to shifts in central blood mass and myocardial electrophysiological responses, respiration information, emotions, skin conductance, Photoplethysmography (PPG), oxygen saturation, electrocardiography (ECG), electroencephalography(EEG), muscle activity (EMG), accelerometer, EOG, temperature, blood glucose, systolic contraction, systemic resistance and cardiac output, each of the plurality of bio-markers projected on one or more screens for viewing by the other one or more users.

16. The system as recited in claim 12, wherein a first type of pain monitoring scales from the set of pain monitoring scales is utilized for assessing the change in the intensity of pain for a first set of users of the one or more users belonging to an age category of adult patients, wherein the first type of pain monitoring scales comprises any accepted pain scale comprising a Visual Analog Scale (VAS), a Verbal Numeric Rating Scale (VNRS), a Brief Pain inventory (BPI), a behavioral pain scale (BPS), a descriptor differential scale (DDS), a dolorimeter pain index (DPI), a neck pain and disability scale and a Visual Descriptive System (VDS).

17. The system as recited in claim 12, wherein a second set type of pain monitoring scales from the set of pain monitoring scales is utilized for assessing the change in the intensity of pain for a second set of users of the one or more users belonging to an age category of pediatric patients, wherein the second type of pain monitoring scales comprises any accepted pediatric pain monitoring scale comprising a physician defined scale, a neonatal pain agitation and sedation scale (N-PASS), a pain assessment tool (PAT), a bernese pain scale for one or more neonates (BPSN), a Wong-Baker scale and a face, legs, activity, crying, and consolability (FLACC) scale.

* * * * *